(12) United States Patent
Williams et al.

(10) Patent No.: US 10,064,606 B1
(45) Date of Patent: Sep. 4, 2018

(54) SPECIMEN COLLECTION AND PRESERVATION APPARATUS

(71) Applicant: SPECTRUM SOLUTIONS L.L.C., Draper, UT (US)

(72) Inventors: Kevin Gregg Williams, Draper, UT (US); Bryan Tapocik, Highland, CA (US); Gregory W. Fitch, Highland, CA (US); William Michael Phillips, Draper, UT (US)

(73) Assignee: SPECTRUM SOLUTIONS L.L.C., Draper, UT (US)

( * ) Notice: Subject to any disclaimer, the term of this patent is extended or adjusted under 35 U.S.C. 154(b) by 324 days.

(21) Appl. No.: 14/952,712

(22) Filed: Nov. 25, 2015

(51) Int. Cl.
*A61B 10/00* (2006.01)
*A61F 13/38* (2006.01)
*A61B 10/02* (2006.01)

(52) U.S. Cl.
CPC .......... *A61B 10/0096* (2013.01); *A61B 10/02* (2013.01); *A61F 13/38* (2013.01)

(58) Field of Classification Search
CPC .......... A61B 10/02; A61F 13/15; A61F 13/38; G01N 1/02; G01N 2001/028; C12M 1/30
USPC .................................................. 600/569, 572
See application file for complete search history.

(56) References Cited

U.S. PATENT DOCUMENTS

| | | |
|---|---|---|
| 3,712,296 A | 1/1973 | Gradone |
| 3,792,699 A * | 2/1974 | Tobin ................. A61B 10/0096 401/133 |
| 3,800,781 A | 4/1974 | Zalucki |
| 3,966,558 A | 6/1976 | Calva-Pellicer |
| 4,311,792 A * | 1/1982 | Avery .................... C12M 45/22 15/144.4 |
| 4,877,037 A | 10/1989 | Ko et al. |
| 5,266,266 A * | 11/1993 | Nason ................ A61B 10/0096 422/411 |
| 7,482,116 B2 | 1/2009 | Birnboim |
| 7,993,871 B2 | 8/2011 | Skiffington et al. |
| 8,696,595 B2 | 4/2014 | Sangha et al. |
| 8,728,414 B2 | 5/2014 | Beach et al. |
| 9,523,115 B2 | 12/2016 | Birnboim |
| 9,732,376 B2 | 8/2017 | Oyler et al. |
| 2003/0143752 A1* | 7/2003 | Feldsine ................ G01N 21/76 436/164 |
| 2004/0014237 A1* | 1/2004 | Sugiyama .......... A61B 10/0096 436/174 |
| 2006/0216196 A1* | 9/2006 | Satoh .................... B01L 3/5029 422/400 |
| 2008/0058676 A1 | 3/2008 | Yong |

(Continued)

FOREIGN PATENT DOCUMENTS

CN 203101085 7/2013

*Primary Examiner* — Michael C Stout
(74) *Attorney, Agent, or Firm* — Workman Nydegger

(57) ABSTRACT

A collection apparatus having an open central retaining member retaining a frustum-shaped cap at one end with a collection vial removably affixed to the frustum-shaped cap. The open central retaining member also retains within it a capsule retaining member into which a frangible capsule retaining a sample preservative if retained. The seal is broken and specimen preservative flows over a collection swab, with the frustum-shaped cap serving as a closing member and an interior wall of the collection vial serving as a closing member at an opposite end of the open central retaining member.

5 Claims, 13 Drawing Sheets

(56) References Cited

U.S. PATENT DOCUMENTS

| | | | |
|---|---|---|---|
| 2008/0260581 A1* | 10/2008 | Rosman | B01L 3/5029 422/68.1 |
| 2009/0023219 A1* | 1/2009 | Perez | A61B 10/0096 436/18 |
| 2011/0021950 A1 | 1/2011 | Daniels | |
| 2012/0220043 A1* | 8/2012 | Sangha | G01N 1/02 436/174 |
| 2014/0051178 A1* | 2/2014 | Niggel | B01L 3/5029 436/164 |
| 2014/0194777 A1 | 7/2014 | Scampini et al. | |

* cited by examiner

SPECIMEN COLLECTION AND PRESERVATION APPARATUS

BACKGROUND OF THE INVENTION

1. Field of the Invention

The present invention relates to the field of collection and preservation of specimens such as biological samples and retaining the collected samples in a safe condition until the biological samples are transferred to a facility for analysis.

2. Description of the Prior Art

The following 11 utility patents and published patent applications are the closest prior art references known to the inventors.

1. U.S. Pat. No. 3,712,296 issued to Frank P. Gradone on Jan. 23, 1973 for "Swab Device for Medical Specimens" (hereafter the "Gradone Patent");
2. U.S. Pat. No. 3,800,781 issued to Kazimierz Zalucki on Apr. 2, 1974 for "Specimen-Taking Device" (hereafter the "Zalucki Patent");
3. U.S. Pat. No. 3,966,558 issued to Cesar Calva-Pellicer on Jun. 29, 1976 for "Device for Collection of Samples for Microbiological Studies" (hereafter the "Calva-Pellicer Patent");
4. U.S. Pat. No. 4,877,037 issued to Su-sen Ko et al. on Oct. 31, 1989 for "Tissue or Mucus Sampling Device" (hereafter the "Ko Patent");
5. United States Published Patent Application No. 2008/0058676 to Peter A. K. Yong on Mar. 6, 2008 for "Retractable Segmented Bio-Molecular Collector Swab System" (hereafter the "Yong Published Patent Application");
6. United States Published Patent Application No. 2011/0021950 to Robert L. Daniels on Jan. 27, 2011 for "Cell Collector" (hereafter the "Daniels Published Patent Application");
7. U.S. Pat. No. 7,993,871 issued to Richard T. Skiffington et al. on Aug. 9, 2011 for "Sampling Method and Device" (hereafter the "Skiffington Patent");
8. U.S. Pat. No. 8,696,595 issued to Jangbir Sangha on Apr. 15, 2014 for "Unitized System for Collection, Drying Transport and Analysis" (hereafter the "Sangha Patent");
9. U.S. Pat. No. 8,728,414 issued to Michael Beach et al. on May 20, 2014 (hereafter the "Beach Patent");
10. United States Published Patent Application No. 2014/0194777 to Steven A. Scampini et al. on Jul. 10, 2014 for "Swab Assembly for Specimen Collection" (hereafter the "Scampini Published Patent Application");
11. Chinese Patent No. CN203101085 to Jun Li et al. on Jul. 31, 2013 for "Cotton Swab Brush for Collecting Livestock Samples" (hereafter the "Li Chinese Patent").

The Gradone Patent discloses the concept of a telescoping sleeve member so that the portion that is being grasped is a portion of the telescoping sleeve which can be extended without having to touch the swab on which the specimen is taken.

The Zalucki Patent discloses a retaining tube into which another tube is press fit retained and presumably locked with a locking mechanism and a specimen gathering portion retained within the inner tube. The specimen gathering portion is then removed from the outer tube and then extended to gather the specimen from the tip which is then placed back into the external cylinder and then locked therein for retention.

The Calva-Pellicer Patent disclose a device for collecting samples for microbiological studies in which a holder, or stopper member, is provided having a rod extending therefrom to which a cotton swab, or the like, can be connected. The holder, or stopper member, includes a first region adapted for sealing engagement with the neck of an inner container, or tube, surrounding the swab to keep the swab in a sterile condition. An outer container, or tube, is also provided which surrounds the inner container and which is also adapted for sealing engagement with the holder, or stopper member.

The Ko Patent discloses a sample member which is retained within a tube and then removed after the sample has been obtained and placed back into the tube. This patent discloses the concept of having the sampling device within the tube so that the sample can be taken and then immediately placed back into the tube.

The Yong Published Patent Application discloses a segmented collector swab which includes a skewer and a plurality of absorbent pads in the assembly on a skewer used for collection of specimens.

The Daniels Published Patent Application discloses a device for a cell collector. The patent application discloses the collector for things such as a pap smear and it has the mechanism by which the device to collect the sample can be extracted and pushed out of the tube to collect the sample and then retracted back into the tube in a lower section where the DNA is located.

The Skiffington Patent discloses a device that has a test tube with a mechanism by which the swab can be used to obtain the specimen and then retracted by a rotational mechanism back into the tube.

The Sangha Patent discloses a unitized system for collection, drying transport and analysis. The patent discloses:

"A specimen collection, drying and transport apparatus comprising: a specimen collector comprising: a specimen collection swab, said swab connected to a shaft having a first shaft end with said specimen collection swab thereon and a second shaft end connected to a closure, said closure having first and second stopper structures extending from opposed sides of a central member The Scampini Published Patent Application discloses a swab assembly for specimen collection.

The Li Chinese Patent discloses an experiment article, and in particular relates to a cotton swab brush for collecting livestock samples. The cotton swab brush comprises a cotton head and a rod, wherein the cotton head comprises a spherically flexible fiber brush head fixed at one end of the rod, a cotton layer is arranged outside the brush head, the rod consists of an extension rod and a sleeve pipe, the cotton head is arranged at one end of the extension rod and the other end of the extension rod is sheathed with the sleeve pipe, and a plurality of transverse notches are formed in the extension rod.

The Beach Patent discloses a closure for a container having a closure body having a first cylindrical portion and a second cylindrical portion opposite the first cylindrical portion. The closure also has a connector disposed in at least one of the first or second cylindrical portions. The connector is adapted to connect one of a sample collection device and an applicator to the closure. The apparatus includes the closure, a container, and optionally one of a sample collection device with an applicator. The collection device is not telescoping. The closure body includes a blocking wall within the closure body preventing liquid from traveling through the apparatus after a specimen has been collected and retained in the container.

There is a significant need for an improved specimen collection apparatus which enables the entire apparatus to be packaged in one single apparatus which facilitates ready collection of the specimen and ready preservation of the specimen in a laboratory vial after the specimen has been collected.

SUMMARY OF THE INVENTION

The present invention is a specimen collection and preservation apparatus. By way of example, the present invention is used for the collection and preservation of biological specimens or samples. The collected specimens include DNA from suspects believed to be involved in a crime, DNA to determine ancestry of a person, and collection of specimens of many different biological animal, human and plant specimens for analysis of the specimen and/or used for research.

Specifically, this invention is an apparatus to collect a biological specimen such as a DNA sample and enclose that sample for preservation until testing is to be performed on that sample.

It is an object of the present invention to have a collection device that can capture and retain the sample and store the sample safely in a closed end vial connected to a first end of a joining or central retaining member with a closing cap affixed at an opposite or second end of the joining or central retaining member.

It is a further object of the present invention to include a collection assembly having an open central retaining member retaining at a second end a closing cap which has a sloping exterior wall with the slope extending downwardly from adjacent the central retaining member to a distal closed end, also described as a frustum-shaped cap. Initially, the collection vial is removably affixed to the frustum-shaped cap, either through a snap fit or a press fit. The open central retaining member is integrally formed with the closing cap which also includes a capsule retaining member into which a frangible capsule retaining a sample preservative liquid is retained. The open central retaining member also retains a specimen collection device at a first end.

It is also an object of the present invention to have a swab which is a collection device to be affixed to the distal end of a telescoping member having several telescoping sections with a telescoping retaining member which is affixed to the first end of the open central retaining member. Since the collection swab is located at the distal end of the telescoping member, this enables the collection device to be extendable to enable the swab to reach into deeper locations such as the back of a person's mouth. The telescoping member can also be retracted after the specimen is collected on the swab.

It is an additional object of the present invention to have an end cap (with sloping exterior wall or frustum shaped) integrally formed with the central retaining member at the second end of the central retaining member. A standard sized laboratory vial has a closed end and an open end by which it is retained on the sloping outer wall of the frustum-shaped cap. The standard sized laboratory vial has a reduced interior chamber to facilitate the requirement of the collection swab. The frustum-shaped cap may have an exterior retaining member and the open end of the standard sized laboratory vial can have a mating member so that the standard sized laboratory vial is snap fit retained on the frustum-shaped cap. Alternatively, the exterior wall of the sloping end cap can be smooth so that the standard sized laboratory vial is press fit retained on the end cap. After the sample is collected, the standard laboratory vial (interchangeably referred to as "vial" or laboratory vial) is detached from its snap fit or press fit on the frustum-shaped or sloping wall end cap and the interior of the vial is placed over the swab and pushed against the swab to cause a retraction of the telescoping member.

It is a further object of the present invention to provide a preservation or buffering solution for the sample to protect the integrity of the sample prior to testing. Preservation liquids are typically chemical solutions high in salts such as ethylenediaminetetraacetic acid (EDTA). It is common in the industry of specimen preservation to allow the collected sample to be washed and sit in this preservation liquid prior to testing. Thus, it is within the spirit and scope of this invention to include EDTA as well as other preservation liquids within the frustum-shaped cap.

It is a further object of the present invention for the preservation liquid solution to be stored in a frangible capsule until after the sample is collected. Once the sample is collected, the laboratory vial is removed from its snap fit or press fit removable retention against the frustum-shaped end cap and placed over the swab and pushed against the swab to retract or close the telescoping member. The telescoping member includes a retaining section retained on the first end of the central retaining member. The retaining section slidably retains a first telescoping section having a piercing member at a proximal end and an opening at its distal end to receive a proximal end of second telescoping section having a distal end to receive a proximal end of a third telescoping section which retains the specimen collection swab at its distal end. As the telescoping member is collapsed, the first telescoping section is retracted into frangible capsule retaining member and the piercing member pierces the frangible capsule so that the preservation liquid flows out of the frangible capsule and flows into the end cap. The specimen collection swab is pushed into the end cap and into the preservation liquid. The entire assembly is sealed with the laboratory vial at one end and the end cap at the opposite end so that the assembly can be shaken to fully mix the preservation liquid into the specimen collection swab. The central retaining section has no blocking wall so that preservation liquid can flow through the central retaining section from the laboratory vial to the frustum-shaped cap. The telescoping retaining section includes openings to permit the preservation liquid to flow through it.

When the telescoping section of the apparatus is completely collapsed, the invention can be sealed for safe keeping and transportation.

It is still a further object of the present invention to have the laboratory vial perform multiple functions. The laboratory vial serves as a handle when the sample is collected. Then, the laboratory vial is used as a cover that fits over the collected sample. The laboratory vial is then used to collapse the telescoping portion of the apparatus. Finally, external threads located on the front exterior surface of the laboratory vial provide a mechanism to seal the laboratory vial into receiving threads in the first end of the central retaining member. The telescoping retaining member is snap fit onto the exterior of the first end of the central retaining member so that the laboratory vial is within the telescoping retaining member, thereby requiring the holes in the telescoping retaining member.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated.

DETAILED DESCRIPTION OF EMBODIMENTS OF THE PRESENT INVENTION

Although specific embodiments of the present invention will now be described with reference to the drawings. it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Figure 1:
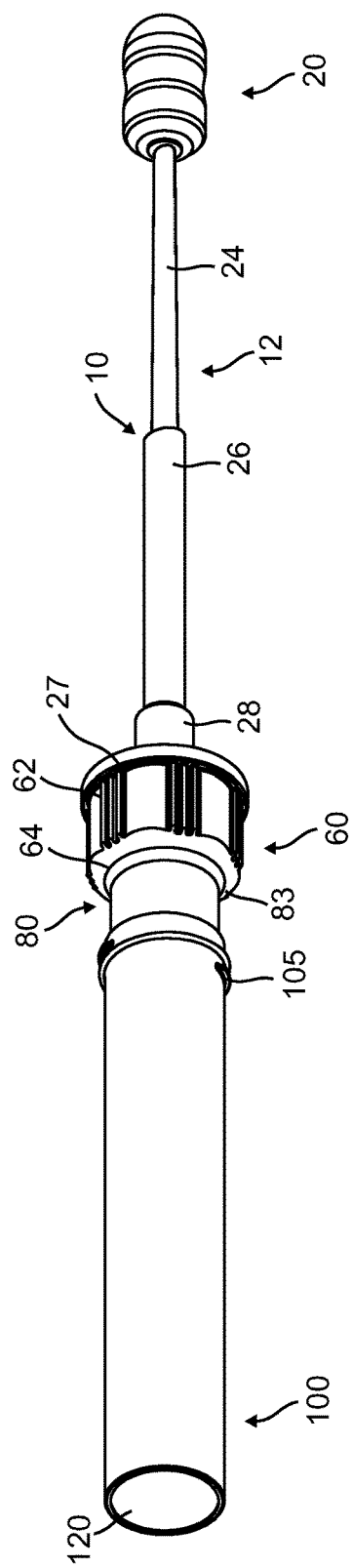
FIG. 1 is a side perspective elevational view of the fully assembled specimen collection assembly with telescoping member fully extended, the preservation swab exposed, the telescoping member retained at one end of the central retaining member, the end cap integrally formed with an opposite end of the central retaining member, and the laboratory vial removably retained on the outer wall of the end cap.
Figure 2:
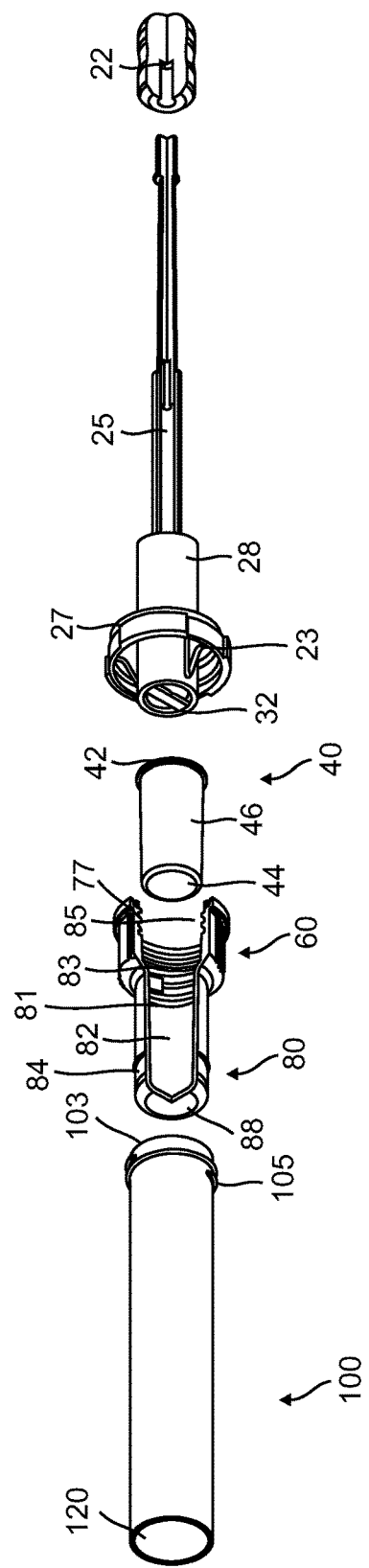
FIG. 2 is a side perspective exploded view of the specimen collection assembly illustrated in FIG. 1.

Referring to FIGS. 1 and 2, illustrated is the present invention specimen collection assembly 10 having a central retaining member 60 which is integrally formed to an cap 80 having a closed distal end 88. The end cap 80 can be frustum shaped or have an exterior sloping wall 83 which is sloping at a reduced diameter from the central retaining member 60 to distal closed end 88. The interior of cap 80 also functions as a cap housing or frangible capsule retaining member 82. The frangible capsule 40 has a distal end 44 and an exterior surface 46 with frangible seal 42 adjacent second end 64 of the central retaining member 60 and also adjacent an open end 81 of end cap 80. The end cap 80 has an exterior wall 83 having a circumferential locking member 84.

The interior of the central retaining member 60 has a hollow interior chamber 79 with threads 83 on the interior chamber wall 77 to the exterior threads 105 of vial 100. The frangible capsule 40 is retained in the interior 82 of end cap 80 which also served as a frangible capsule retaining member. The frangible capsule 40 retains the specimen preservation liquid 45 (see FIG. 16).

The telescoping member 12 includes a telescoping retaining member 27 containing interior walls 23 to which is press fit or snap fit retained on first end 64 of the central retaining member 60. FIGS. 1 and 2 also illustrate specimen collection swab 20 which is extendable and retractable by extending or retracting the first telescoping section 24 and a second telescoping section 26 and a third telescoping section 28 away from or towards telescoping retaining member 27. The telescoping member 12 includes a retaining section 27 retained on the first end 62 of the central retaining member 60 and a first telescoping section 28 having a piercing member 32 at a proximal end and an opening at its distal end to receive a proximal end of second telescoping section 26 having a distal end to receive a proximal end of a third telescoping section 24 which retains the specimen collection swab 20 at its distal end. When the specimen collection apparatus 10 is removed from the package, the telescoping member 12 including sections 28, 26 and 24 can be extended, or are already extended for convenience when collecting a biological specimen with specimen collection swab 20.

This is an important feature of the present invention by allowing the user to extend first telescoping stem or section 28, second telescoping stem or section 26 and a third telescoping stem 24 to more easily obtain the desired specimen. This is a unique innovation of the present invention by providing the user a longer and more versatile reach when collecting the specimen. This extendable and retractable feature is also important in the retractable stage for reducing the size of the apparatus for storage. After the specimen is collected and third telescoping stems 24, second telescoping stem 26 and the first telescoping stem 28 are retracted, the apparatus becomes smaller and thus more cost effective to transport. This also is a very important feature given the rising costs of transportation and shipping.

Laboratory vial 100, as illustrated in FIG. 1, is a standard laboratory vial used for testing purposes. The size of this vial is a well known size and those skilled in the art are familiar with its use and size. During the collection process, laboratory vial 100 is used as a handle to allow the user to hold the specimen collection apparatus 10. While being held by laboratory vial 100, the user can more easily extend and aim specimen collection swab 20 or specimen collector 20 to the desired location and extract a biological specimen.

Figure 3:
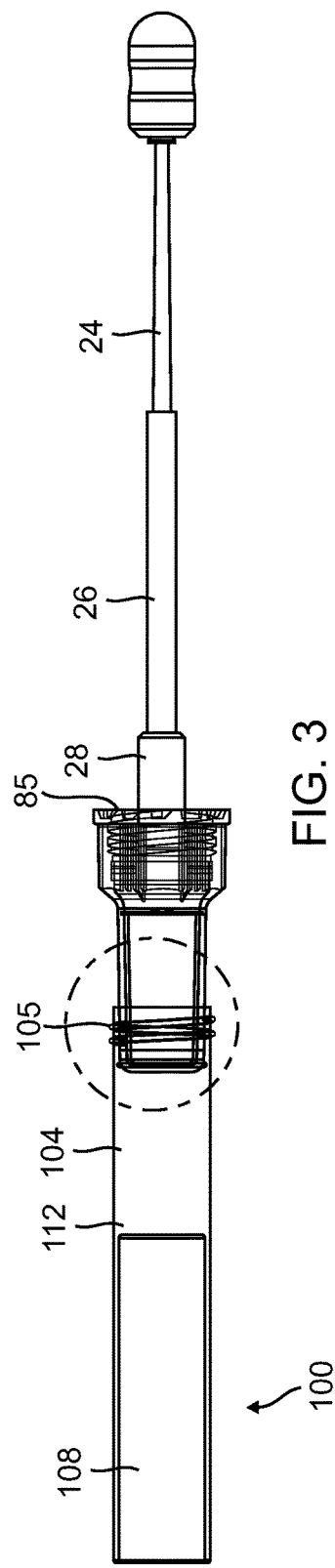
FIG. 3 is a partially transparent view of the specimen collection assembly illustrated in FIG. 1.
Figure 4:
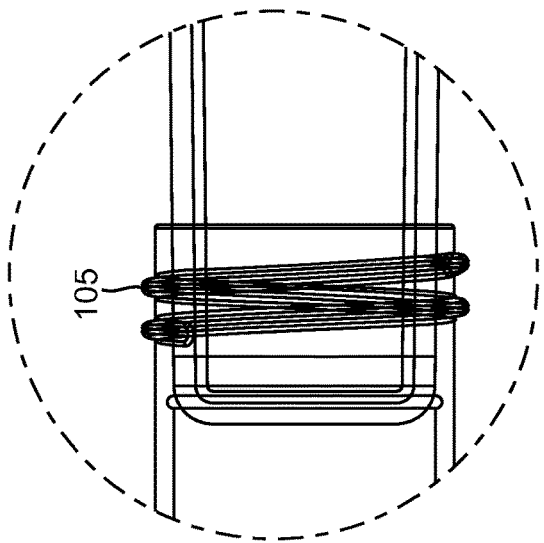
FIG. 4 is a close-up side elevational view of a portion of the specimen collection assembly with and the external threads on the laboratory vial shown in greater detail.
Figure 5:
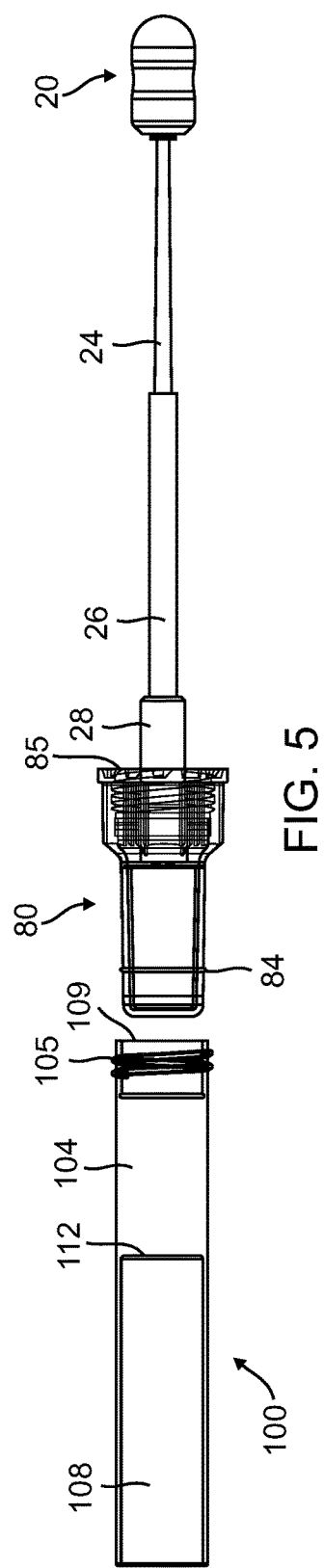
FIG. 5 is a side elevational partially exploded view of the specimen collection assembly with the telescoping elements extended and with laboratory vial removed from the end cap.

Referring to FIG. 3, the laboratory vial 100 has an internal wall 112 that separates first cylindrical chamber 104 from second cylindrical chamber 108. Vial 100, as previously stated, is a standard sized vial used in laboratories. First cylindrical chamber 104 is sized to retain specimen collector swab 20 after the biological specimen is collected. Second cylindrical chamber 108 is the remainder of the unused interior chamber space in laboratory vial 100 and is not used in conjunction with the first cylindrical chamber 104. It is used because the standard sized laboratory vial 100 is most frequency used by the test laboratories to which the specimen collection apparatus 10 and collected specimen is used.

The specimen collection assembly 10 includes an open central retaining member 60 integrally formed at a second end 64 with end cap 80 serving as a capsule retaining member in interior chamber 82 into which a frangible capsule 40 retaining a sample preservative 45 is retained.

The swab 20 which is a collection device is affixed to the distal end of a telescoping retaining member which in turn is affixed to a first end 62 of the central retaining member 60. Since the collection swab is located at the distal end of the telescoping member 12, this enables the collection device to be extendable to enables the swab 20 to reach into deeper locations such as the back of a person's mouth. The telescoping member 12 can also be retracted after the specimen is collected on the swab 20. The standard sized laboratory vial 100 is press fit retained on a sloping outer wall 83 of end cap 80. After the sample is collected, the vial 100 is detached from its press fit on the frustum-shaped cap 80, or snap fit retained by circumferential ring 84 on frustum-shaped cap engaging interior mating member 103 adjacent the front opening 109 of the laboratory vial 100. The laboratory vial 100 has a closed distal end 120.

Referring to FIGS. 3 through 16, after a specimen is collected on swab 20, the laboratory vial 100 is disengaged from its snap fit or press fit retention on outer wall 83 of frustum-shaped cap 80 and the interior 104 of the laboratory vial 100 is placed over the collection swab 20 and pushed against the swab to cause a retraction of the telescoping member 12 as previously discussed.

Figure 16:
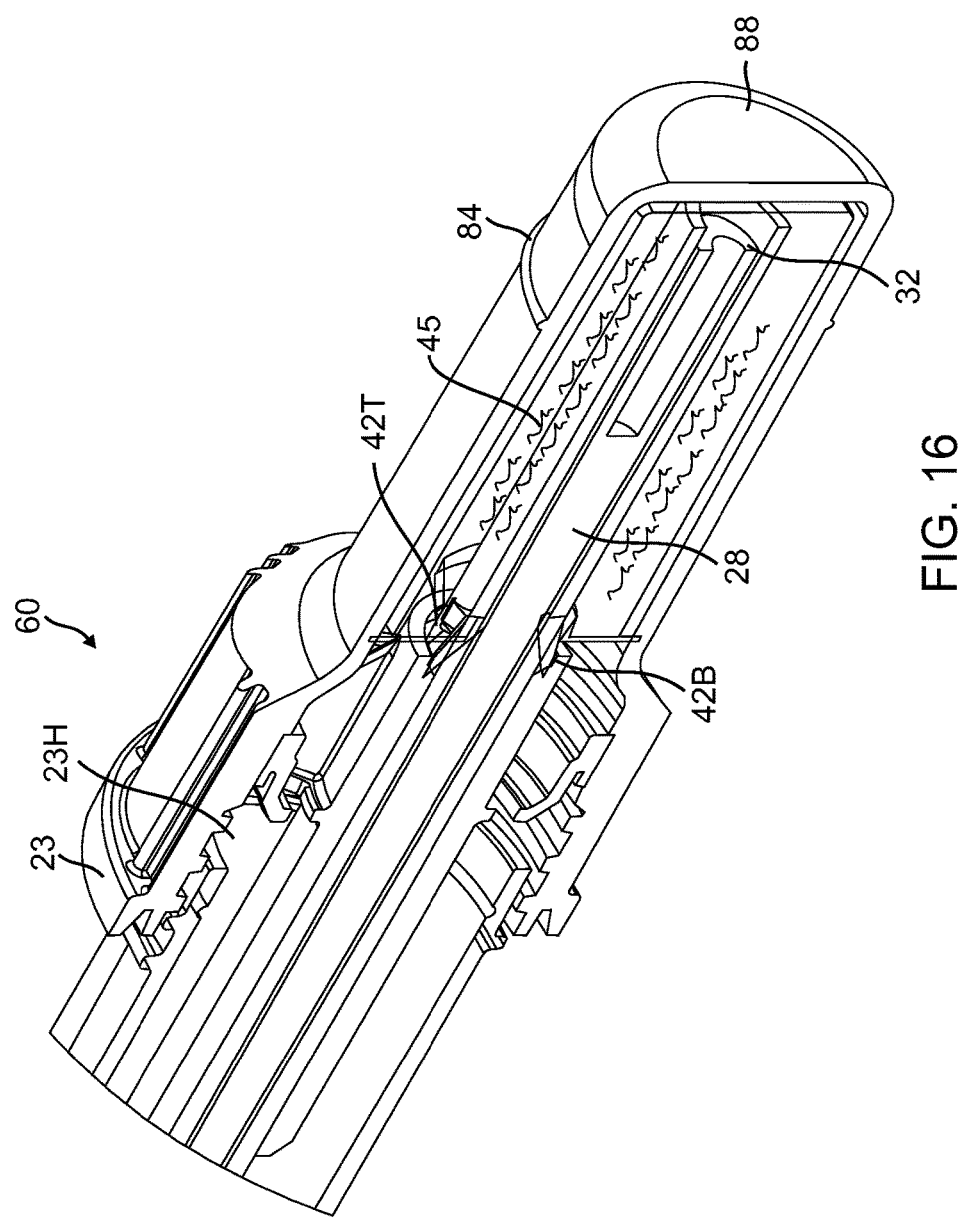
FIG. 16 is a cross sectional view of cross section 16-16 shown in FIG. 14 illustrating the frangible capsule retaining the specimen collection liquid being ruptured.

The preservation liquid 45 is stored in the frangible capsule 40 until after the sample is collected. Once the sample is collected, the laboratory vial 100 is removed from its press fit or snap fit retention, against the frustum-shaped cap 80 and the its front opening 109 of interior chamber 104 is placed over the collection swab 20 and pushed against the swab to retract or close the telescoping member 12. The telescoping member 12 includes a retaining section 27 retained on the first end 62 of the central retaining member 60 and a first telescoping section 28 having a piercing member 32 at a proximal end and an opening at its distal end to receive a proximal end of second telescoping section 26 having a distal end to receive a proximal end of a third telescoping section 24 which retains the specimen collection swab 20 at its distal end. As the telescoping member is collapsed, the first telescoping section 28 is retracted into frangible capsule retaining member 82 and the piercing member 32 pierces the frangible capsule 40 so that the preservation liquid 45 flows out of the frangible capsule 40 and flows into the end cap 80. The specimen collection swab 20 is pushed into the end cap 80 and into the preservation liquid 45. The entire assembly is sealed with the laboratory vial 100 at one end and the end cap 80 at the opposite end so that the specimen collection apparatus can be shaken to fully mix the preservation liquid 45 onto the specimen collection swab 20. The central retaining section 60 has no blocking wall so that preservation liquid 45 can flow through the central retaining section 60 from the laboratory vial 100 to the frustum-shaped cap 80. As illustrated in FIG. 16, the telescoping retaining member 23 which is retained on exterior 62 of central retaining member 60 has openings 23H to enable the preservation liquid 45 to flow through it.

Figure 6:
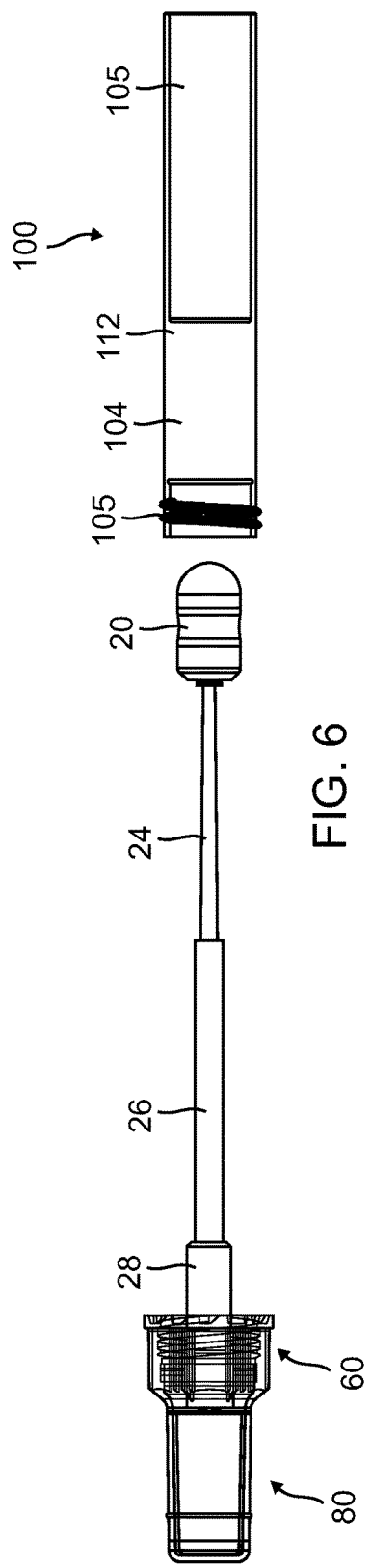
FIG. 6 is a side elevational view of the specimen collection assembly with telescoping elements extended after the specimen collection swab has been used and with laboratory vial removed from the end cap and in position to be placed over the specimen collection swab and telescoping sections of the telescoping member.
Figure 7:
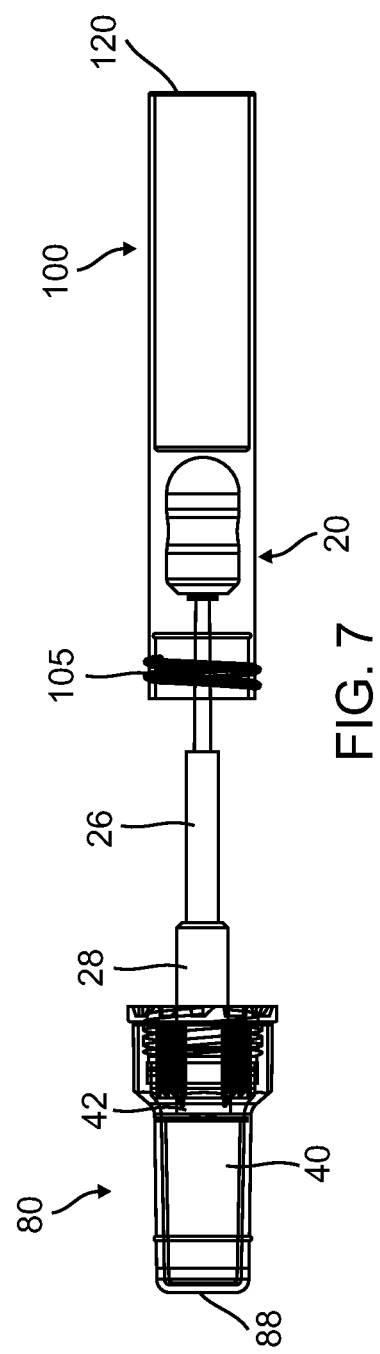
FIG. 7 is a side elevational view of the specimen collection assembly illustrating the telescoping sections collapsing when the laboratory vial is placed over specimen collection swab and pushed towards the central retaining member.
Figure 8:
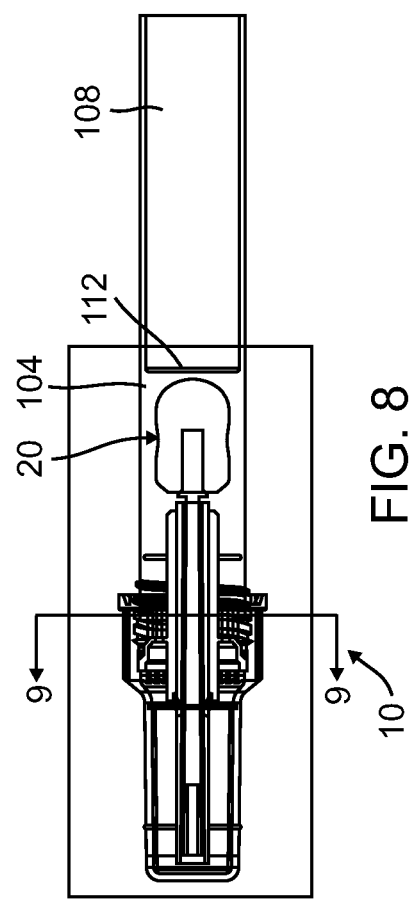
FIG. 8 is a side elevational view of the specimen collection assembly with the telescoping sections collapsed, and the laboratory vial closed over specimen collection swab.
Figure 9:
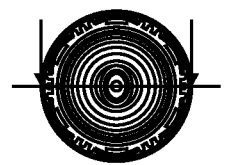
FIG. 9 is a cross sectional view taken along line 9-9 of FIG. 8.
Figure 10:
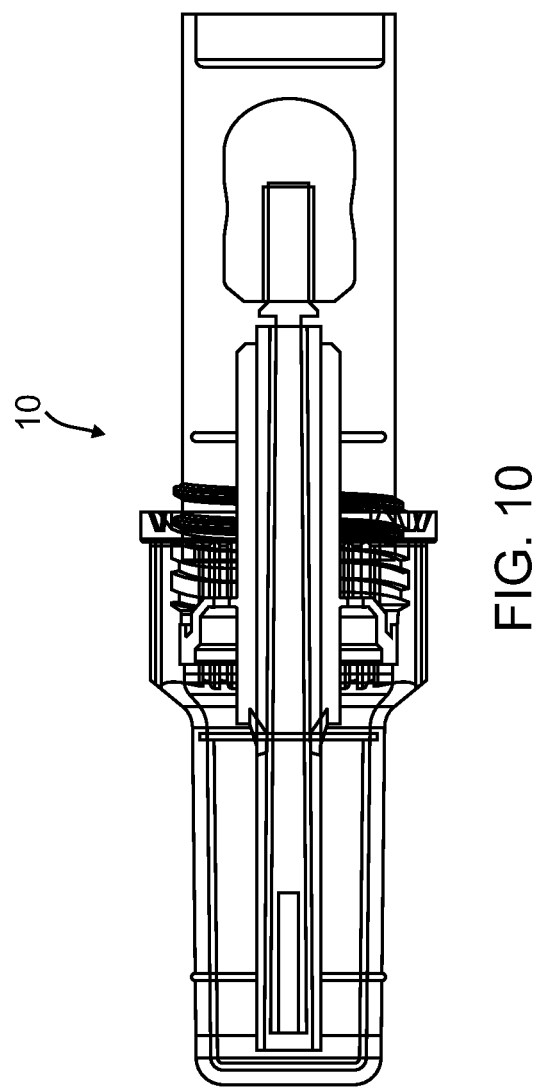
FIG. 10 is a close-up view of FIG. 8 showing a side elevational view with the telescoping elements collapsed and the laboratory vial closed over the specimen collection swab and the threaded sections of the central retaining member and the laboratory vial threaded together.
Figure 11:
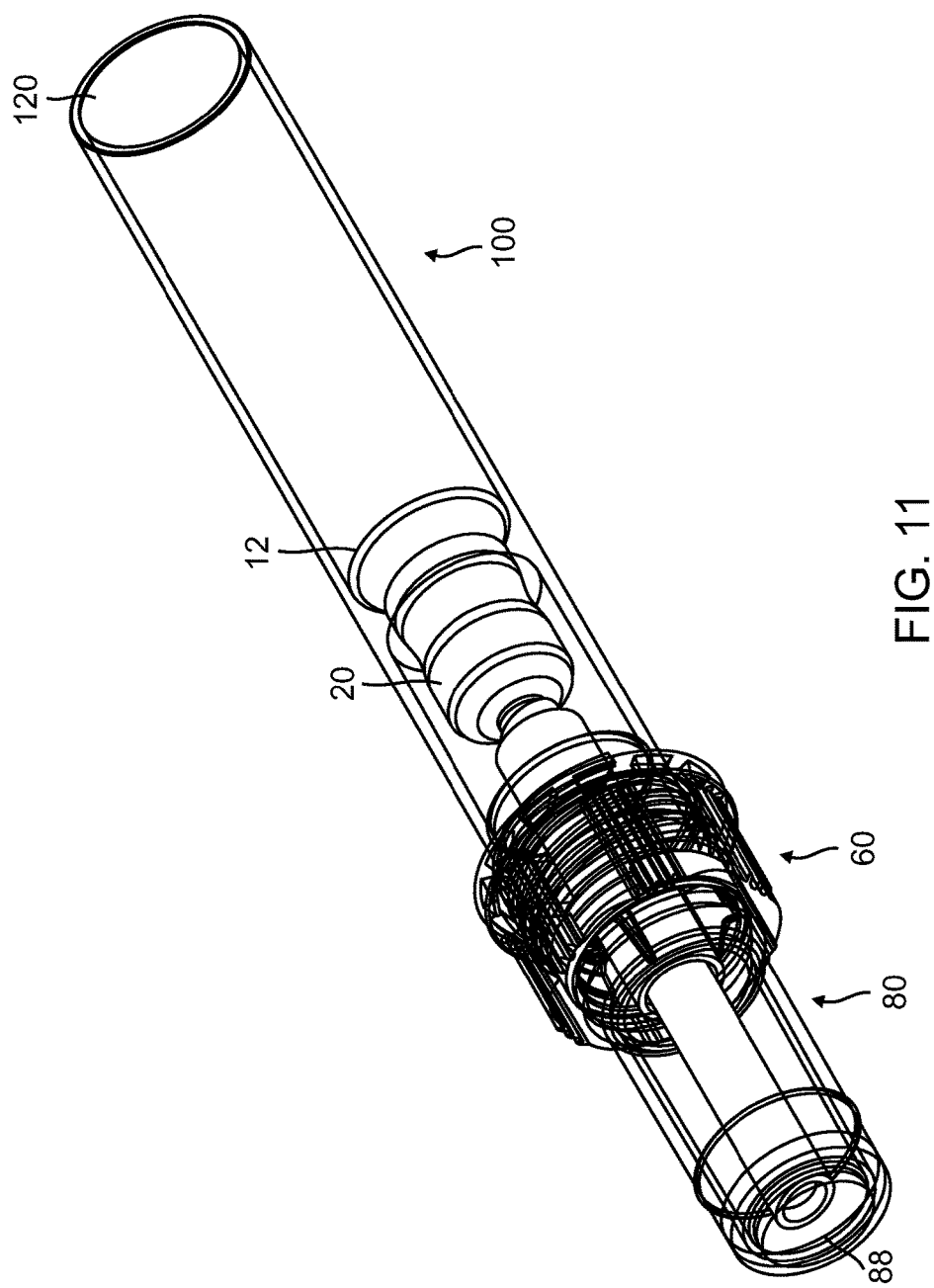
FIG. 11 is a side perspective view illustrating the telescoping elements collapsed and the laboratory vial closed over the specimen collection swab and the threaded sections of the central retaining member and the laboratory vial threaded together, illustrated the end cap serving as an opposite side closing member.

When the telescoping section of the apparatus is completely collapsed the invention can be sealed for safekeeping and transportation. Once the specimen has been collected, laboratory vial 100 can be removed from the press fit connection to frustum-shaped cap 80 as illustrated in FIG. 6. Vial 100 is then flipped 180 degrees to allow vial opening 109 (see FIG. 5) to fit over specimen collector 20 as illustrated in FIGS. 7 and 8. Specimen collector 20 can then be placed into first cylindrical chamber 104 of vial 100 until specimen collector 20 presses against internal wall 112 as illustrated in FIG. 8. The laboratory vial 100 pushes on the telescoping member as described to collapse the telescoping sections.

Figure 13:
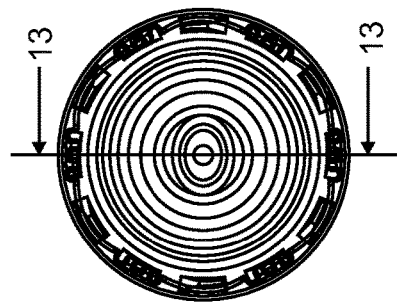
FIG. 13 is a cross sectional view of cross section 13-13 shown in FIG. 14.
Figure 12:
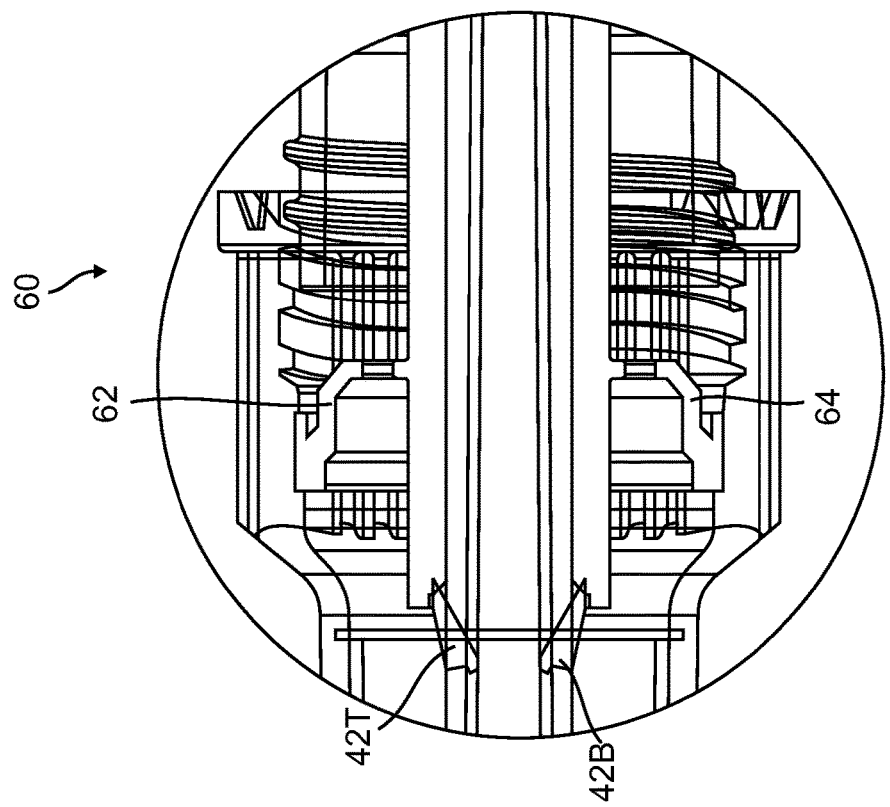
FIG. 12 is a close-up view of the central joining member with the frangible preservation liquid capsule punctured.
Figure 14:
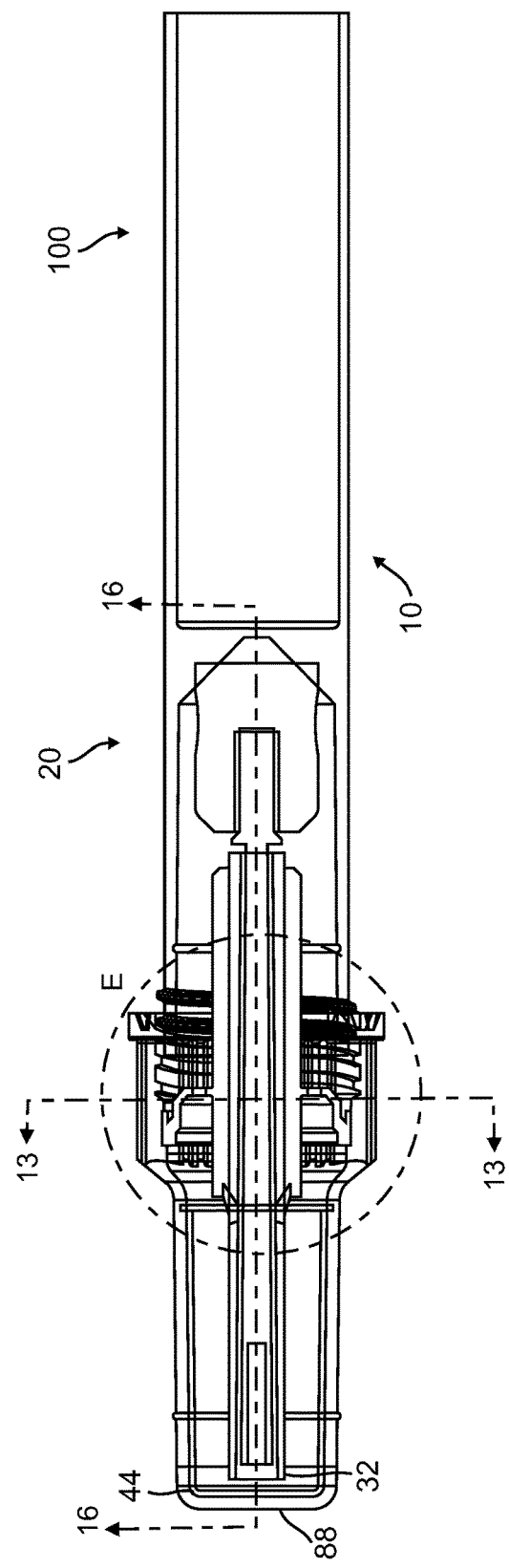
FIG. 14 is a side view of the specimen collection assembly fully closed.
Figure 15:
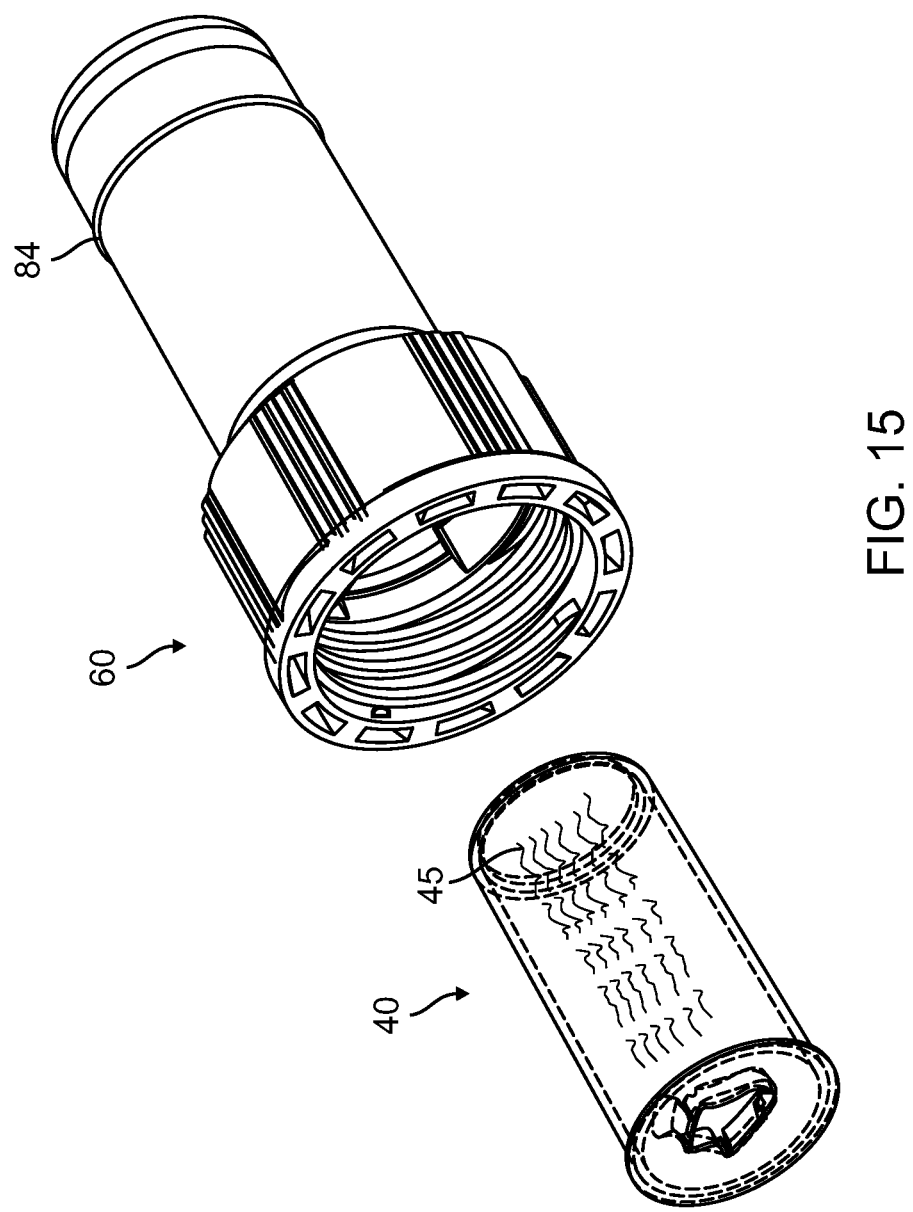
FIG. 15 is a close up perspective view of the central retaining member showing internal threads on an open side which is used to engage mating external threads on an exterior surface of the laboratory vial, the right portion of FIG. 15 illustrating the end cap integrally formed at an opposite end of the central retaining member, and the frangible capsule which holds the preservation liquid retained within the central retaining member illustrated away from the central retaining member on the left portion of FIG. 15.

As illustrated in FIGS. 5 through 16, when telescoping collection swab 20 is retracted and closed, third telescoping stem 24 compresses into a second stem 26 interior chamber 25 and second telescoping stem 26 compresses into a first stem 28. When second telescoping stem 26 is completely inside of first stem 28, piercing members 32 of first stem 28 ruptures frangible capsule 40. Then, as the user continues to compress telescoping collection member 12 and rotates vial 100, piercing members 32 pass through frangible seal 42 of frangible capsule 40 releasing preservation liquid 45. As illustrated if FIG. 12, the ruptured frangible seal 62 is broken into two parts. The top portion of the ruptured frangible seal is top seal 42T and the bottom portion of the ruptured frangible seal is bottom seal 42B as illustrated in FIGS. 12 and 13. The rupturing of frangible seal 42 releases preservation liquid 45 which is allowed to flow through interior open central retaining member 60. Preservation liquid 45 is allowed to pass through these openings and flow to specimen collector 20.

After rupturing frangible seal 42, piercing members 32 passes through frangible capsule 40 until it reaches the bottom 88 of end cap 80 While the piercing member 32 is approaching frangible capsule bottom 44, the user can rotate vial 100 to allow external threads 105 on vial 100 to interlock with internal threads 83 inside central retaining member 60 to close and seal the present invention specimen collection apparatus 10.

In the closed condition as illustrated in FIGS. 8, 10, 11, 14, and 16 specimen collection assembly or apparatus 10 can be shaken or rotated from upright to bottom end up to allow the preservation liquid to flow through the entire interior of central retaining member 60. Closed end 88 of end cap 80 and internal wall 112 of laboratory vial 100 form the limits of the entire interior chamber where the preservation liquid 45 can flow after the biological specimen is collected and the invention is closed by having external threads 105 interlock with internal threads 83.

In this closed condition, the invention described here within is protected from the outside atmosphere by being air and water tight. This reduces the chances of the sample being contaminated and helps to maintain the integrity of the collected specimen during transportation to the laboratory.

Of course the present invention is not intended to be restricted to any particular form or arrangement, or any specific embodiment, or any specific use, disclosed herein, since the same may be modified in various particulars or relations without departing from the spirit or scope of the claimed invention herein above shown and described of which the apparatus or method shown is intended only for illustration and disclosure of an operative embodiment and not to show all of the various forms or modifications in which this invention might be embodied or operated.

What is claimed is:

1. A collection apparatus, comprising:
   a. a hollow central retaining member which is integrally formed at a second end to an end cap having a closed distal end and an open proximal end aligned with an opening in the hollow central retaining member, a frangible capsule containing liquid specimen preservative is retained in a frangible capsule retaining member which is also an interior chamber of said end cap, the end cap having a sloping exterior wall with a reduced diameter from adjacent the hollow central retaining member to a distal closed end of the end cap, the sloping exterior wall of the end cap having a circumferential locking member;
   b. a telescoping member including a telescoping retaining member affixed to a first end of said hollow central retaining member, the telescoping member further including a first section slidably retained within the telescoping retaining member and having a piercing member at a proximal end and an opening at a distal end thereof to receive a proximal end of a second telescoping section, the second telescoping section having an opening at a distal end thereof to receive a proximal end of a third telescoping section, which retains a specimen collection swab at a distal end thereof;
   c. a specimen collection vial having a circumferential wall, an open front end, a closed rear end, and an interior dividing wall forming a collection chamber between the open front end, the dividing wall, and the circumferential wall, wherein the specimen collection vial is snap fit retained onto the end cap by the circumferential locking member and an engaging member disposed within the specimen collection vial;
   d. wherein the collection apparatus is configured such that, after a specimen is collected in the collection swab, the specimen collection vial can be removed from the end cap, the collection chamber placed over the collection swab, and a compression force applied to the specimen collection vial to cause the third section, the second section, and the first section of the telescoping member to retract, the open end of the specimen collection vial to be retained in a first end of the hollow retaining member, and retraction of the first section to cause the piercing member to rupture the frangible capsule and release the preservation fluid over the collection swab; and
   e. wherein the collection apparatus is configured to be sealed by the closed end of the end cap at one end and the interior dividing wall of the collection chamber of the specimen collection vial at an opposite end, the telescoping retaining member having interior openings configured to cooperate with the hollow central collection member to enable preservation fluid to flow within the collection chamber, openings in the telescoping retaining member, hollow central retaining member, and the end cap.

2. The collection apparatus in accordance with claim 1, wherein the end cap is frustum shaped.

3. A collection apparatus, comprising:
   a. a hollow central retaining member having a second end which is integrally formed to an end cap with a downwardly sloping exterior wall, the downwardly sloping exterior wall having a widest portion adjacent the hollow central retaining member and having a closed distal end and an open proximal end aligned with an opening in the hollow central retaining member, a frangible capsule containing liquid specimen preservative retained in a frangible capsule retaining member disposed within the interior chamber of said end cap;
   b. a telescoping member including a telescoping retaining member affixed to a first end of said hollow central retaining member, the telescoping member further including at least two telescoping sections, with a first telescoping section slidably retained within the telescoping retaining member and having a piercing member at a proximal end thereof and an opening at a distal end thereof configured to receive a proximal end of a second telescoping section having a distal end comprising a specimen gathering member;
   c. a specimen collection vial having a circumferential wall, an open front end, a closed rear end, and an interior dividing wall forming a collection chamber between the open front end, the dividing wall, and the circumferential wall, wherein the specimen collection vial is removably retained onto the downwardly sloping wall of said end cap;
   d. wherein the collection apparatus is configured such that, after a specimen is collected in the collection member, the specimen collection vial can be removed from the downwardly sloping wall of the end cap, the collection chamber placed over the collection member, and a compression force applied to the specimen collection vial to cause the at least two sections of the telescoping member to retract, the open end of the specimen collection vial to be retained in a first end of the hollow retaining member and retraction of the first section to cause the piercing member to rupture the frangible capsule and release the preservation fluid over the collection member; and
   e. wherein the collection apparatus is configured to be sealed by the closed end of the cap at one end and the interior dividing wall of the collection chamber such that the hollow central collection member enables preservation fluid to flow within the collection chamber, hollow central retaining member, openings in said telescoping retaining member, and the end cap.

4. A specimen collection apparatus comprising:
   a. a central retaining member connected at a first end to a telescoping retaining member and integrally formed at a second end to a frustum-shaped cap;

b. the telescoping retaining member retaining a first telescoping stem having a piercing member extendably connected to a first telescoping stem which is extendably connected to a second telescoping stem which is connected to a third telescoping stem, a distal end of the third telescoping stem retaining a specimen collection member;

c. a laboratory vial removably retained on an exterior wall of said frustum-shaped cap;

d. said laboratory vial having a first internal cylindrical section separated from a second internal cylindrical section by an interior wall, said first internal cylindrical section having an open ended interior chamber sized to retain said specimen collection member, and said first internal cylindrical section having external threads near an opening of said first internal cylindrical section;

e. the central retaining member having a hollow interior with no transverse interior blocking wall;

f. the frustum-shaped cap housing a frangible capsule retaining member, the frangible capsule retaining member housing a frangible capsule comprising a preservation liquid, wherein the frangible capsule is configured to be ruptured by the piercing member as the telescoping member is collapsed;

g. wherein the specimen collection member is configured to be pushed into the frustum-shaped cap to enable the preservation liquid to flow onto the collection swab; and h. wherein the specimen collection apparatus is configured to seal the collected specimen of the specimen collection member within the specimen collection apparatus such that when the specimen collection apparatus is sealed, the specimen collection apparatus comprises a first closed end defined by the closed end of the frustum-shaped cap and a second closed end defined by the interior wall of the laboratory vial.

5. A biological specimen collection device comprising:

a. a first central joining member removably connected at a first end to a proximal end of a multi-section swab retaining member and integrally formed at a second end to a capsule housing member having a frustum-shaped exterior surface with the widest diameter of the capsule retaining member integrally formed with said central joining member and extending at a narrowing slope to a closed distal end;

b. said multi-section swab retaining member affixed to a first telescoping stem which is extendably connected to a second telescoping stem which is connected at a distal end to a specimen collection member;

c. said capsule housing having a frustum-shaped exterior body containing a capsule with said capsule having a circular shaped frangible first wall, a circular shaped second wall opposite the first wall, and a frustum section connecting said first wall and said second wall;

d. a laboratory vial removably retained to the exterior wall of said capsule housing; and e. said laboratory vial having a first cylindrical section separated from a second cylindrical section by an interior wall; with said first cylindrical section having an open ended interior chamber sized to retain said specimen collection member and first cylindrical section having external threads near opening of said first cylindrical section.

* * * * *

UNITED STATES PATENT AND TRADEMARK OFFICE
CERTIFICATE OF CORRECTION

PATENT NO. : 10,064,606 B1
APPLICATION NO. : 14/952712
DATED : September 4, 2018
INVENTOR(S) : Williams et al.

Page 1 of 1

It is certified that error appears in the above-identified patent and that said Letters Patent is hereby corrected as shown below:

In the Specification

<u>Column 6</u>
Line 36, change "79" to –85–

<u>Column 7</u>
Line 63, remove [its]

Signed and Sealed this
Sixth Day of November, 2018

Andrei Iancu
*Director of the United States Patent and Trademark Office*